United States Patent
Hill

[11] Patent Number: 5,876,416
[45] Date of Patent: Mar. 2, 1999

[54] SURGICAL KNIFE

[76] Inventor: Frank C. Hill, 10 Brandywine La., Columbia, S.C. 29206

[21] Appl. No.: 924,271
[22] Filed: Sep. 5, 1997
[51] Int. Cl.⁶ .................................................. A61B 17/32
[52] U.S. Cl. ............................ 606/167; 606/180; 30/186
[58] Field of Search ..................... 606/167, 170, 606/179, 180; 30/27, 186, 440

[56] References Cited

U.S. PATENT DOCUMENTS

| | | |
|---|---|---|
| D. 370,532 | 6/1996 | Epstein et al. . |
| 3,798,688 | 3/1974 | Wasson . |
| 3,906,626 | 9/1975 | Riuli . |
| 4,414,974 | 11/1983 | Dotson et al. . |
| 4,473,076 | 9/1984 | Williams et al. . |
| 4,898,170 | 2/1990 | Hofmann et al. . |
| 5,078,724 | 1/1992 | Takase . |
| 5,178,623 | 1/1993 | Cinberg et al. . |
| 5,203,865 | 4/1993 | Siepser . |
| 5,254,130 | 10/1993 | Pncet et al. ............................... 606/206 |
| 5,258,002 | 11/1993 | Jeffers et al. . |
| 5,320,635 | 6/1994 | Smith ....................................... 606/180 |
| 5,352,233 | 10/1994 | Anis . |
| 5,370,652 | 12/1994 | Kellan . |
| 5,487,745 | 1/1996 | McKenzie . |
| 5,501,700 | 3/1996 | Hirata . |
| 5,522,829 | 6/1996 | Michalos ................................. 606/170 |
| 5,549,637 | 8/1996 | Crainich .................................. 606/207 |
| 5,643,294 | 7/1997 | Tovey et al. ............................. 606/148 |

*Primary Examiner*—Michael Buiz
*Assistant Examiner*—Daphna Shai
*Attorney, Agent, or Firm*—Michael A. Mann; Nexsen Pruet Jacobs & Pollard LLP

[57] ABSTRACT

A surgical knife especially suited for surgical procedures such as a tympanoplasty comprises a handle having a proximal and a distal end, with a curved blade rotatably carried on a post on the distal end of the handle. The blade extends radially outward from the post and beyond the end of the post in roughly an "S" shape. The cutting edge of the blade is on the end of the "S" and is thus spaced apart from and beyond the end of the post, where it can swivel about the axis of the post. When cutting, the blade will follow the direction the handle is moved, swiveling into alignment with that direction by the pressure of the tissue it is cutting.

14 Claims, 2 Drawing Sheets

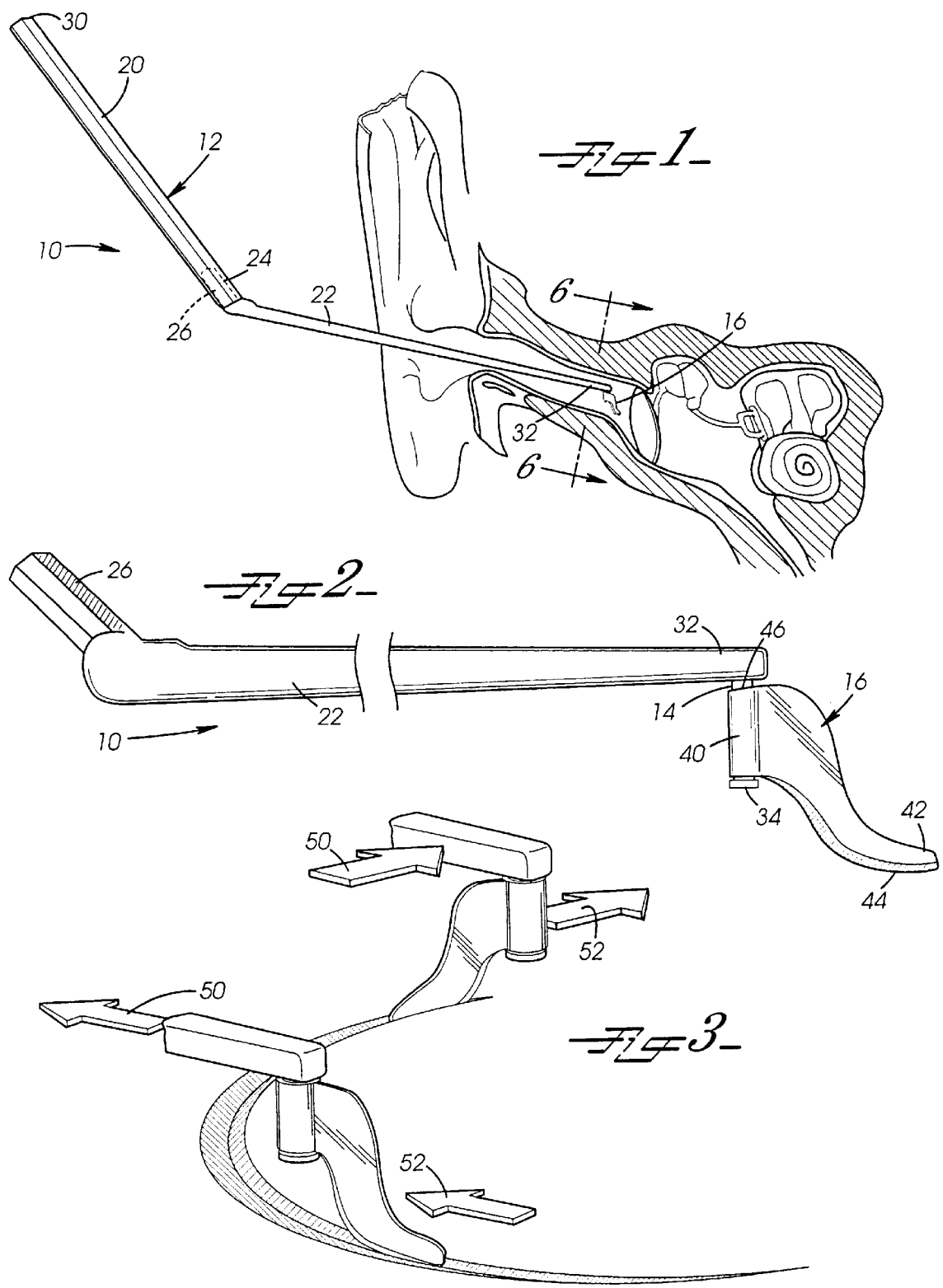

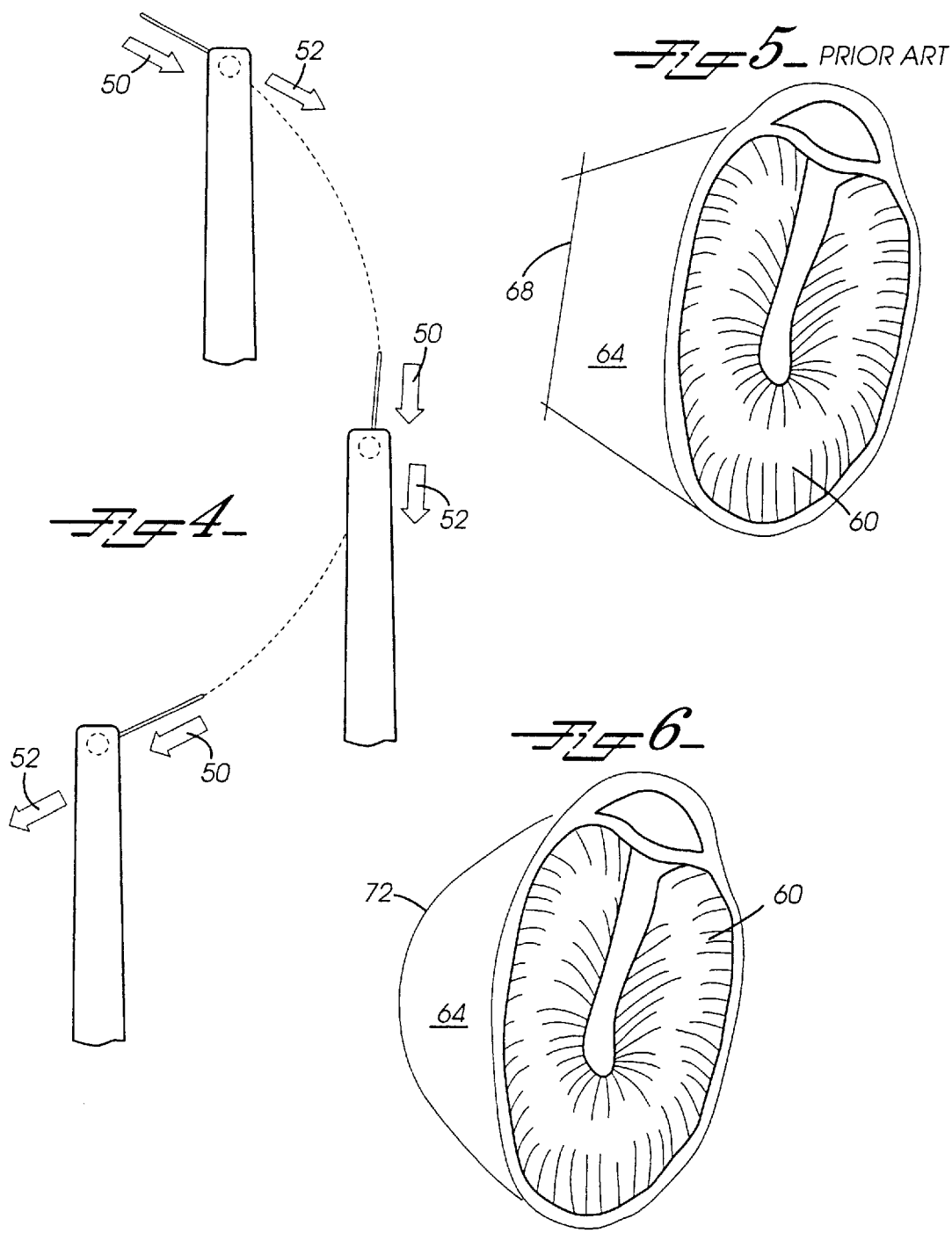

SURGICAL KNIFE

BACKGROUND OF THE INVENTION

1. Field of the Invention:

The present invention relates to surgical knives and blades. More specifically, the present invention relates to surgical knives for use in making small, curved incisions where there is little room to maneuver, such as in the ear.

2. Discussion of Background:

Surgery in the middle ear requires access to the portion of the ear behind the tympanic membrane, or "eardrum," from the exterior of the ear. Cutting the eardrum is disfavored as a way to provide this access because the eardrum is under tension, so the time for it to heal following surgery and the quality of healing suggest alternative routes would be preferred. The alternate route is to cut the ear tissue adjacent to the eardrum, making three, separate straight cuts that intersect to form three sides of a box or "U," leaving the fourth side in place to permit easier reattachment of the cut sides. The severed tissue can be elevated to provide access to the middle ear. This type of procedure is used as part of a tympanoplasty or a stapedectomy.

There are a number of surgical knives, including double-bladed knives, roller knives and flap knives. However, none of these knives is suitable for making an efficient cut around the eardrum.

SUMMARY OF THE INVENTION

According to its major aspects and briefly recited, the present invention is a surgical knife comprising a handle, a post attached to one end of the handle and having an axis roughly perpendicular to the major axis of the handle, and an arcuate blade attached to the post so that it swivels about the axis of the post.

The replaceable blade has a somewhat "S" shaped or slipper-shaped profile, with the curved portion of the cutting edge located radially outward from and longitudinally beyond the end of the post, so that the cutting edge swivels around the axis of the post, remaining parallel to a radius. To cut tissue, the handle is placed roughly parallel to the surface to be cut and the curved blade brought into engagement with the skin so that it penetrates the skin. The convex-curved edge will slice through the tissue with significant mechanical advantage as the handle is moved and the blade is held in engagement with the tissue.

The curved blade is designed so that when the handle is pulled or pushed as the blade is cutting into tissue, the pressure of the tissue against the sides of the blade causes the blade to swivel into alignment with the direction that the handle is moving. When the direction of movement of the handle is changed, the blade automatically swings into alignment with the new direction. When the handle is moved along a curved path, the blade will follow the curved path of the handle.

The ability to follow a curved path is the aspect of the blade that is the most significant feature of the invention. With it, a curved incision can be made around the eardrum rather than three separate cuts as in the prior art method. The curving is the result of the combined effect of the swiveling blade, the spacing of the blade with respect to the post about which it swivels, and the blade's curved shape. The fact that the blade swivels is essential to its being able to change direction without changing the orientation of the handle. The spacing means that more tissue will act against the portion of the blade inside the turn to cause it to swivel. Finally, the curve of the blade allows it to slice down into the tissue as it moves (like the prow of a ship through water) rather than be dragged through the tissue, thus providing a better mechanical advantage and a smoother incision.

These and other features and their advantages will be apparent to those skilled in the art of surgical knives from a careful reading of the Detailed Description of Preferred Embodiments accompanied by the following drawings.

BRIEF DESCRIPTION OF THE DRAWINGS

In the drawings,

FIG. 1 is a perspective view of a surgical knife according to a preferred embodiment of the present invention shown in an ear canal;

FIG. 2 is a perspective view of a portion of the surgical knife showing part of the handle and the blade, according to a preferred embodiment of the present invention;

FIG. 3 is a detailed perspective view of the blade of the surgical knife of FIG. 2 making a curved incision;

FIG. 4 is a top view of a portion of the blade of the present surgical knife tracing a curved path for a curved incision;

FIG. 5 is an illustration of an ear drum showing the prior art incisions around the ear drum for a surgical procedure that will take place in the middle ear; and FIG. 6 is an illustration of an ear drum showing a curved incision around the ear drum performed using a surgical knife, according to the present invention.

DETAILED DESCRIPTION OF PREFERRED EMBODIMENTS

Referring now to FIGS. 1–4, the present invention is a surgical knife 10 comprising a handle 12 with a post 14 and a blade 16. Handle 12 is preferably fashioned in two parts, a first portion 20 and a second portion 22. First portion 20 has a recess 24 formed in it to receive a corresponding end 26 of second portion 22, which is formed in such a way that second portion 22 can be firmly secured in first portion 20. Preferably, first and second portions 20, 22, fit together in a number of ways and at an angle with respect to each other, so that blade 16 can be oriented with respect to handle 12 in a comfortable, convenient way for use by the surgeon. For example, recess 24 can be a hexagonal hole and the end of second portion 22 hexagonally shaped to fit into the hexagonal hole of first portion 20. This combination will allow the angle of the blade with respect to the handle to be set at six different orientations.

When the two portions 20, 22 of handle 12 are put together, handle 12 has a proximal end 30 and a distal end 32. At distal end 32 is post 14 with an axis approximately perpendicular to the long axis of handle 12. Post 14 has a circular cross section and is preferably hollow to receive a threaded end cap 34 of larger diameter than the main portion of post 14. Blade 16 can be replaced after use by unscrewing end cap 34 and sliding blade 16 from post 14.

Attached to post 14 is blade 16. Blade 16 has a first end 40 and a second end 42. Second end 42 carries a cutting edge 44 that is curved concave outward, meaning away from post 14 and handle 12, so that it takes on an "S" shape. A circular hole 46 is formed in first end 40 of blade 16 that is dimensioned to fit rotatably over post 14 so that blade 16 will swivel freely about post 14. Preferably first end 40 is long enough so that hole 46 is a long cylinder that will rotate stably about post 14 and not wobble.

Second end 42 with cutting edge 44 is spaced apart from post 14 both radially and axially from endcap 34 of post 14, so that cutting edge 44 revolves around post 14 when blade 16 swivels and so that when blade 16 is penetrating tissue, post 14 is just above the tissue. Preferably, cutting edge 44 is about one and one-half millimeters from the axis of post 14 and about one and one-half millimeters from end cap 34 of post 14.

When cutting edge 44 has penetrated tissue and handle 12 is being pulled in a direction, the pressure of the tissue on the sides of the cut will cause blade 16 to align itself with the direction that the handle is being pulled, that is, the direction of handle 12 can be characterized by a line lying parallel to a plane defined by the face of blade 16. The direction handle 12 is being pulled does not mean the orientation of the handle, but rather the line defined by the same point on handle 12 in two close moments in time. If handle 12 is moving in through a curve, as illustrated especially in FIGS. 3 and 4, the direction of handle 12 is constantly changing but not necessarily its orientation, which may in fact not change at all, as suggested in FIGS. 3 and 4. This feature is important in ear surgery because the handle orientation is constrained by the ear canal. The direction handle 12 is moving is indicated by arrows. Arrows 50 indicate the direction of handle 12 and arrows 52 indicate the direction of blade 16. No matter whether handle 12 is moving in a straight or curved line, blade 16 will align itself by swiveling with that direction.

Furthermore, because blade 16 has a convex-curved cutting edge 44, the incision is made with good mechanical advantage, which is important in making a smooth straight cut rather than a jagged cut or tearing the tissue. A smooth, straight cut generally heals better and with less scar tissue.

FIGS. 5 and 6 illustrate, respectively, a prior art incision and an incision possible with the present invention in the context of surgery in the middle ear. The present invention is ideally suited for making small curved incisions, especially in tight quarters such as in the ear canal. In these figures there is shown an ear drum 60 and the surrounding tissue 64. An incision is made to define a flap 68 of surrounding tissue 64 that can then be elevated to allow access to the middle ear. This general technique is used, for example, in tympanoplasty and stapedectomy procedures. According to the prior art, three straight, intersecting incisions are made to form the flap, as illustrated in FIG. 5. Using the present surgical knife 10, a curved incision can be made in one motion to make a curved flap 72.

It will be apparent to those skilled in the art of surgical knives that many changes and substitutions can be made to the foregoing detailed description without departing from the spirit and scope of the invention, which is defined by the appended claims.

What is claimed is:

1. A surgical knife for cutting tissue, comprising:

a handle having a distal end;

a rigid post carried by said distal end, said post having a longitudinal axis throughout the entire length of said post, such that said longitudinal axis is perpendicular to said handle;

a blade rotatably mounted to said post and having a cutting edge, said cutting edge of said blade being spaced apart from said post so that said blade swivels around said post.

2. The surgical knife as recited in claim 1, wherein said cutting edge is displaced axially with respect to the end of said post.

3. The surgical knife as recited in claim 1, wherein said cutting edge is convex.

4. The surgical knife as recited in claim 1, wherein said post is approximately one millimeter in length.

5. The surgical knife as recited in claim 1, wherein said cutting edge extends up to approximately one and one-half millimeters beyond said post.

6. The surgical knife as recited in claim 1, wherein said post is approximately one millimeter in length, and said cutting edge extends up to approximately one and one-half millimeters beyond said post.

7. A surgical knife for cutting tissue, comprising:

a handle having a distal end;

a rigid post carried by said distal end, said post having a longitudinal axis throughout the entire length of said post, such that said longitudinal axis is perpendicular to said handle;

a blade rotatably mounted to said post and having a curved cutting edge, said cutting edge of said blade being spaced radially and axially apart from said post so that said blade swivels around said post and extends beyond said post.

8. The surgical knife as recited in claim 7, wherein said handle has a first portion and a second portion, said first portion having means formed therein for receiving said second portion in locking relationship.

9. The surgical knife as recited in claim 7, wherein said post is approximately one millimeter in length.

10. The surgical knife as recited in claim 7, wherein said cutting edge extends up to approximately one and one-half millimeters beyond said post.

11. The surgical knife as recited in claim 7, wherein said post is approximately one millimeter in length, and said cutting edge extends up to approximately one and one-half millimeters beyond said post.

12. A surgical knife for cutting tissue, comprising:

a handle having a first portion and a second portion, said first portion having means formed therein for receiving said second portion in locking relationship;

a rigid post carried by said second portion, said post having a longitudinal axis throughout the entire length of said post, such that said longitudinal axis is perpendicular to said handle;

a blade rotatably mounted to said post and having a cutting edge, said cutting edge of said blade being spaced radially approximately one and one-half millimeters from said axis of said post so that said blade swivels around said post.

13. The surgical knife as recited in claim 12, wherein said cutting edge extends approximately one and one-half millimeters from the end of said post.

14. The surgical knife as recited in claim 12, wherein said cutting edge is curved.

* * * * *